(12) United States Patent
Hasebe et al.

(10) Patent No.: US 8,969,805 B2
(45) Date of Patent: Mar. 3, 2015

(54) TERAHERTZ WAVE MEASUREMENT DEVICE AND METHOD

(71) Applicants: Takayuki Hasebe, Tokyo (JP); Hitoshi Tabata, Tokyo (JP); Shigeru Kitamura, Kyoto (JP)

(72) Inventors: Takayuki Hasebe, Tokyo (JP); Hitoshi Tabata, Tokyo (JP); Shigeru Kitamura, Kyoto (JP)

(73) Assignees: The University of Tokyo, Tokyo (JP); ARKRAY, Inc., Kyoto (JP)

( * ) Notice: Subject to any disclaimer, the term of this patent is extended or adjusted under 35 U.S.C. 154(b) by 0 days.

(21) Appl. No.: 13/857,249

(22) Filed: Apr. 5, 2013

(65) Prior Publication Data

US 2014/0097344 A1    Apr. 10, 2014

(30) Foreign Application Priority Data

Oct. 9, 2012  (JP) ................................. 2012-224555

(51) Int. Cl.
*G01J 5/02* (2006.01)
*G01N 21/59* (2006.01)
*G01N 21/01* (2006.01)
*G01N 21/3581* (2014.01)
*G01N 21/552* (2014.01)

(52) U.S. Cl.
CPC ............... *G01N 21/59* (2013.01); *G01N 21/01* (2013.01); *G01N 21/3581* (2013.01); *G01N 21/552* (2013.01)
USPC .................................................. 250/339.06

(58) Field of Classification Search
USPC ....................................... 250/339.06, 454.11
See application file for complete search history.

(56) References Cited

U.S. PATENT DOCUMENTS

| | | | | |
|---|---|---|---|---|
| 8,610,071 | B2* | 12/2013 | Kamba et al. | 250/339.07 |
| 2006/0231762 | A1* | 10/2006 | Ohtake et al. | 250/341.8 |
| 2008/0314152 | A1* | 12/2008 | Ouchi | 73/597 |
| 2009/0123978 | A1* | 5/2009 | Takagi | 435/91.5 |
| 2009/0302223 | A1* | 12/2009 | Tamada et al. | 250/340 |
| 2009/0314944 | A1* | 12/2009 | Evans et al. | 250/341.8 |
| 2010/0220327 | A1* | 9/2010 | Kiwa et al. | 356/432 |
| 2011/0205528 | A1* | 8/2011 | Ogawa et al. | 356/51 |
| 2012/0153159 | A1* | 6/2012 | Kamba et al. | 250/341.3 |
| 2013/0037721 | A1* | 2/2013 | Ouchi | 250/353 |

FOREIGN PATENT DOCUMENTS

| | | | |
|---|---|---|---|
| GB | 2482378 A | * | 2/2012 |
| JP | 2007-078621 A | | 3/2007 |
| WO | 2010/044193 A1 | | 4/2010 |

* cited by examiner

*Primary Examiner* — David J Makiya
*Assistant Examiner* — Taeho Jo
(74) *Attorney, Agent, or Firm* — Morgan, Lewis & Bockius LLP

(57) ABSTRACT

The base plate is transmissive to terahertz waves, and a sample is disposed at the base plate. In the conductive periodic structure, plural transmission portions that transmit terahertz waves are arrayed with a predetermined period. The conductive periodic structure is disposed apart from a position at which the sample is disposed. The waveguide includes a total reflection surface provided at a boundary face with the conductive periodic structure. The total reflection surface totally reflects incident terahertz waves, and the waveguide guides incident terahertz waves toward the total reflection surface. The magnitudes of one or more of a distance between the position at which the sample is disposed and the conductive periodic structure, a property of the base plate, and the predetermined period are set such that a dip showing a characteristic absorption is formed in a predetermined frequency region of a spectrum of terahertz waves.

10 Claims, 17 Drawing Sheets

THz WAVES

THz WAVES

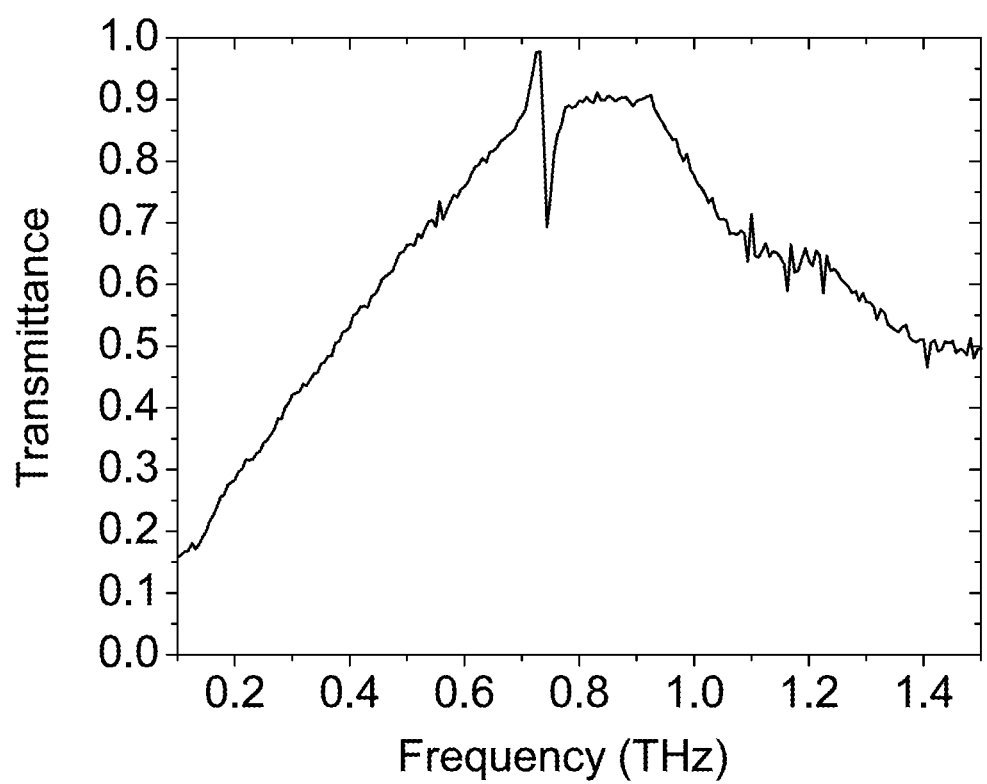

TERAHERTZ WAVE MEASUREMENT DEVICE AND METHOD

CROSS-REFERENCE TO RELATED APPLICATION

This application is based upon and claims the benefit of priority of the prior Japanese Patent Application No. 2012-224555, filed on Oct. 09, 2012, the entire contents of which are incorporated herein by reference.

BACKGROUND OF THE INVENTION

1. Field of the Invention

The present invention relates to a terahertz wave measurement device and method.

2. Description of the Related Art

Currently, for the detection of measurement targets such as biorelated substances at practical levels, detection methods that utilize labelling such as fluorescence and color-emitting enzyme reactions are principally used. However, these detection methods, as well as causing primary antibodies to react, cause secondary antibodies, labelling substances and the like to react, and it is necessary to detect measurement targets from the emitted colors, fluorescence and the like. As a result, labor is required and detection times of several hours or more may be needed. There are also further problems, such as reactive effects due to steric exclusion of labelled molecules and the like. Moreover, there are measurement targets for which labelling is difficult or very expensive. Accordingly, a label-free detection method capable of detecting measurement targets such as biorelated substances and the like without the application of labelling is desired.

Because terahertz waves are in an energy range corresponding to intermolecular oscillations, there are hopes for the application of terahertz waves to label-free detection.

As a sensing device utilizing terahertz waves, a sensing device has been proposed that acquires information about a sample using electromagnetic waves that include a frequency in the frequency range from 30 GHz to 30 THz (for example, see Japanese Patent Application Laid-Open (JP-A) No. 2007-78621). This sensing device is equipped with a conductor portion, a periodic structure disposed at a portion or a vicinity of the conductor portion, and a sample retention portion that retains the sample. In this sensing device, changes in the sample under conditions in which surface plasmon resonance is produced in the vicinity of the sample retention portion when electromagnetic waves interact in the conductor portion are detected. Thus, information about the sample is acquired.

Measurement methods based on attenuated total reflection (ATR) using terahertz waves and measurement methods in which ATR is employed have also been proposed (for example, see the Pamphlet of International Publication No. 2010/044193).

SUMMARY OF THE INVENTION

However, conventional label-free detection using terahertz waves is targeted to the measurement of dry samples. If a measurement target sample is in the form of an aqueous solution, terahertz waves may not pass through the aqueous solution, because the absorption of terahertz waves in water is high.

A technique utilizing ATR is applicable even when a measurement target sample is an aqueous solution. However, the spectrum of terahertz waves that are measured does not show a characteristic peak but is flat, or high-sensitivity measurement of the terahertz waves may not be possible.

The present invention has been made in order to solve the problems described above, and an object of the invention is to provide a terahertz wave measurement device and method that do not require labelling of a measurement target, may measure terahertz waves with high sensitivity, and are applicable even to aqueous solutions.

Solution to Problem

In order to achieve the object described above, the terahertz wave measurement device of the present invention includes: a base plate at which a sample is to be disposed, the base plate being transmissive to terahertz waves; a conductive periodic structure in which a plurality of transmission portions that transmit terahertz waves are arrayed with a predetermined period, at least a surface of the conductive periodic structure being constituted with a conductive material, and the conductive periodic structure being disposed apart from a position at which the sample is disposed; and a waveguide including a total reflection surface provided at a boundary face with the conductive periodic structure, the total reflection surface totally reflecting incident terahertz waves, and the waveguide guiding incident terahertz waves in a direction toward the total reflection surface, wherein the magnitude of at least one of a distance between the position at which the sample is disposed and the conductive periodic structure, a property of the base plate, or the predetermined period is set such that terahertz waves emitted from the waveguide by total reflection at the total reflection surface show a characteristic absorption in a predetermined frequency region. The property of the base plate is, for example, a dielectric constant or refractive index.

The conductive periodic structure may be disposed at the side of a face of the base plate that is opposite to a face thereof at which the sample is disposed.

The base plate and the conductive periodic structure may be disposed in area contact. For example, pressure may be applied to put the base plate and the conductive periodic structure into area contact.

At least one of the base plate and the conductive periodic structure, or the waveguide and the conductive periodic structure may be integrally structured. For example, an integral structure may be formed by vapor deposition of the conductive periodic structure at a surface of the base plate or waveguide, or by printing of a pattern of the conductive periodic structure at the same.

The conductive periodic structure may be sandwiched between the base plate and the waveguide, pressure may be applied, and the base plate and the conductive periodic structure, and the conductive periodic structure and the waveguide may be respectively put into area contact.

The base plate may be structured as a micro-total analysis system (micro-TAS) including a channel in which the sample is disposed. In this case, a structure may be formed in which the channel in the micro-TAS and the conductive periodic structure are spaced apart.

The conductive periodic structure may include a wire grid structure or a metal mesh structure. The waveguide may include a prism. The base plate may include glass or plastic.

The terahertz wave measurement method of the present invention includes: measuring a reference spectrum using the terahertz wave measurement device described hereabove, the reference spectrum including at least one of an amplitude spectrum or a phase spectrum of terahertz waves relating to a reference sample that includes a binder that specifically binds with a measurement target substance; measuring a target spectrum using the terahertz wave measurement device, the target spectrum including at least one of an amplitude spectrum or a phase spectrum of terahertz waves relating to one of a target sample in which the measurement target substance is added to the reference sample, or a target sample in which a content of the measurement target substance is unknown; and performing at least one of detection, identification or characteristic analysis of the measurement target substance on the basis of at least one of a frequency region showing a characteristic absorption or a signal strength at this frequency region in each of the reference spectrum and the target spectrum.

Advantageous Effects of Invention

As described above, according to the terahertz wave measurement device and method of the present invention, effects are provided in that labelling of a measurement target is made unnecessary, terahertz waves may be measured with high sensitivity, and the terahertz wave measurement device and method may be applied even to aqueous solvents.

BRIEF DESCRIPTION OF THE DRAWINGS

FIG. 27 is a graph showing an example of measurement results when the conductive periodic structure in FIG. 26 is employed.

DESCRIPTION OF EMBODIMENTS

Herebelow, exemplary embodiments of the present invention are described in detail, referring to the attached drawings.

—Schematic Structure of the Present Exemplary Embodiments—

First, the general structure of a terahertz wave measurement device in accordance with the present exemplary embodiments is described.

The present exemplary embodiments are based on ATR using terahertz waves. In usual ATR, a sample is put into area contact with a crystal medium that has a large refractive index, an angle of incident light is made larger than the critical angle, and total reflection at a boundary face between the sample and the crystal medium is caused. When total reflection occurs, evanescent waves penetrating into the sample are generated. The evanescent waves are not scattered in a direction perpendicular to the total reflection surface, and have a large electric field amplitude characteristic. Depending on the molecular structure of the sample, the evanescent waves are absorbed by interaction between the molecular structure and the evanescent waves, and the strength of the reflected light is reduced. From measurements of this reflected light, an ATR spectrum is obtained and information about the sample may be acquired.

Small molecules such as amino acids and saccharides have characteristic peaks in the terahertz region spectrum. However, small molecules in an aqueous solution lose their characteristic peak in the terahertz region spectrum. This is because the absorption peak is caused by an intermolecular oscillation mode. Changes in hydration phenomena, aggregate motions of water and suchlike affect the spectrum when an aqueous solution is used as a sample.

Accordingly, a terahertz wave measurement device in accordance with the present exemplary embodiments has a structure in which a conductive periodic structure is provided at the total reflection surface of terahertz waves in ATR. In the conductive periodic structure, plural transmissive portions that transmit terahertz waves are arrayed with a predetermined period. According to this structure, a frequency region that shows a characteristic absorption is formed in a terahertz wave spectrum. Herebelow, the exemplary embodiments are described in detail.

—First Exemplary Embodiment—

Figure 1:
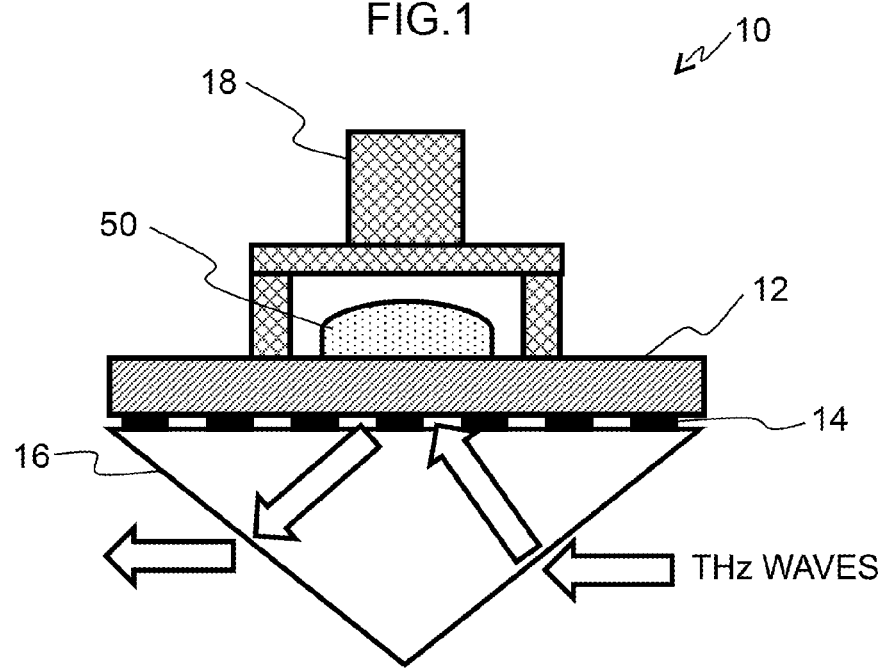
FIG. 1 is a schematic diagram showing a structure of a terahertz wave measurement device in accordance with a first exemplary embodiment.

As shown in FIG. 1, a terahertz wave measurement device 10 in accordance with a first exemplary embodiment includes a base plate 12, a conductive periodic structure 14, a waveguide 16 and a torque wrench 18. A sample 50 is disposed on the base plate 12. In the conductive periodic structure 14, transmissive portions (apertures) that transmit terahertz waves are periodically arrayed. The waveguide 16 is for causing total reflection of terahertz waves at a boundary face between the waveguide 16 and the conductive periodic structure 14. The torque wrench 18 is for fixing the base plate 12, the conductive periodic structure 14 and the waveguide 16 in area contact.

It is sufficient that the base plate 12 be transmissive to terahertz waves and that the sample 50 may be fixed at one face of the base plate 12. For example, glass, plastic or the like may be used for the base plate 12.

Figure 2:
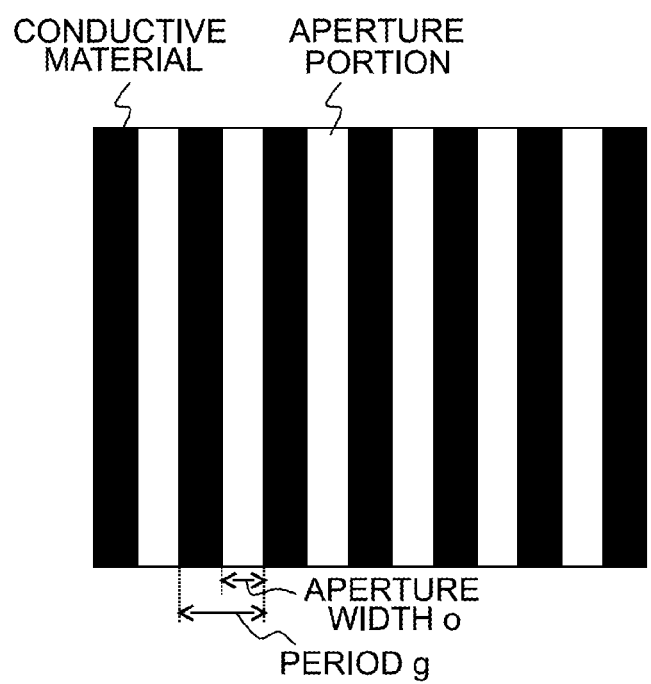
FIG. 2 is a schematic diagram showing the structure of a conductive periodic structure.

As shown in FIG. 2, the conductive periodic structure 14 is a wire grid structure in which conductive members with the same width are arrayed with a predetermined period g, and thus plural transmission portions (apertures) that transmit terahertz waves are arrayed at the predetermined period, each with an aperture width o. It is sufficient if the material of the conductive periodic structure 14 is conductive at least at the surface (not more than around $10^6$ Ω·cm). The material of the conductive periodic structure 14 is not limited to inorganic materials such as metals and semiconductors.

Figure 3:
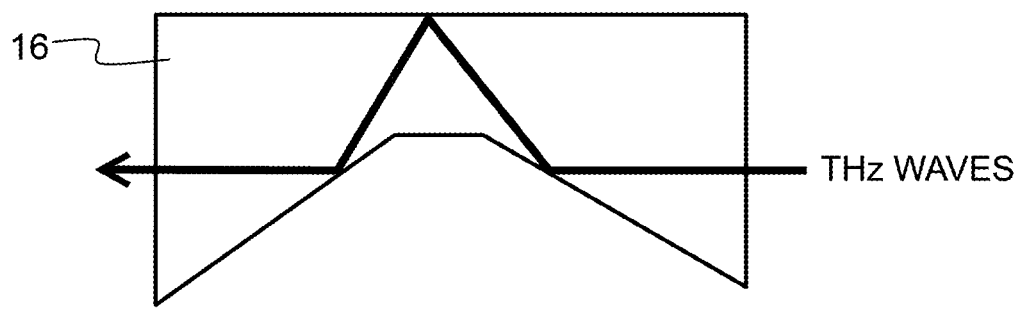
FIG. 3 is a schematic diagram showing another example of the shape of a waveguide.
Figure 4:
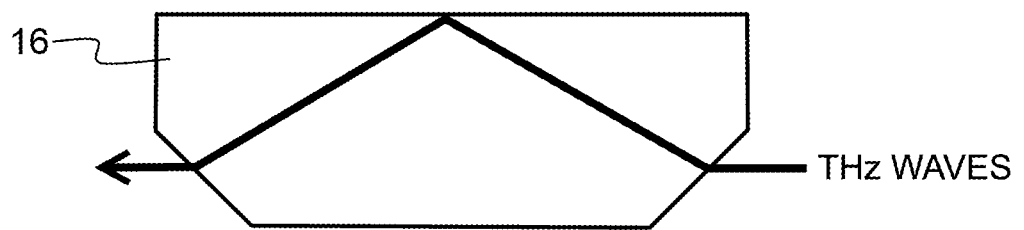
FIG. 4 is a schematic diagram showing yet another example of the shape of the waveguide.

As the waveguide 16, for example, a prism such as a high-resistance silicon Dove prism or the like may be used, but this is not a limitation. It is sufficient that the waveguide 16 structures a total reflection surface for terahertz waves at the boundary with the conductive periodic structure 14. The shape of the waveguide 16 is not limited to the triangular shape in plan view that is shown in FIG. 1. For example, shapes such as those shown in FIG. 3 and FIG. 4 may be used. Herein, cases are described in which the terahertz waves are incident on the waveguide 16 in the p-polarization.

The torque wrench 18 puts the base plate 12 and the conductive periodic structure 14 into area contact and puts the conductive periodic structure 14 and the waveguide 16 into area contact by applying pressure in a state in which the conductive periodic structure 14 is sandwiched between the base plate 12 and the waveguide 16. Because terahertz waves have wavelengths of the order of 30 µm to 3 mm, there is no need for chemical or physical bonding between the base plate 12 and the conductive periodic structure 14 or between the conductive periodic structure 14 and the waveguide 16, and it is sufficient to simply put these into respective area contact. The torque wrench 18 has a structure in which a region in which the sample 50 is placed on the base plate 12 is hollow, and this structure does not affect the measurements of terahertz waves.

Figure 5:
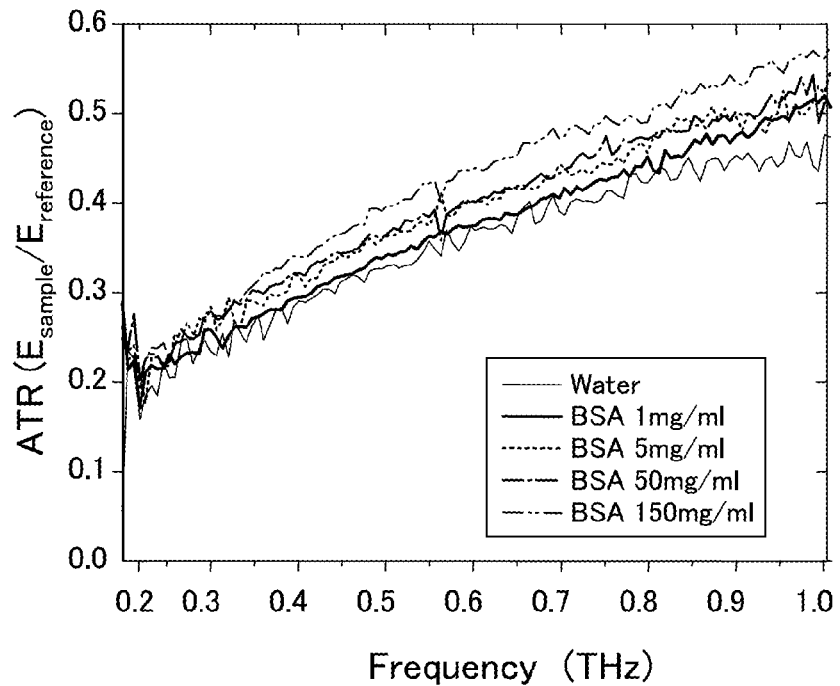
FIG. 5 is a graph showing an example of measurement results of bovine serum albumin (BSA) solutions by conventional ATR.

FIG. 5 shows spectra of terahertz waves in accordance with changes in a concentration of bovine serum albumin (BSA) in an aqueous solution (0 mg/ml (i.e., water), 1 mg/ml, 5 mg/ml, 50 mg/ml, and 150 mg/ml), measured by a conventional ATR technique in which the conductive periodic structure 14 is not employed. The vertical axis of FIG. 5 shows values, which are referred to as ATR hereinafter, in which the energy (strength) $E_{sample}$ of terahertz waves measured from each sample are divided by an energy $E_{reference}$ of terahertz waves acquired when a predetermined base measurement is performed. As shown in FIG. 5, the terahertz wave spectra of BSA in the aqueous solution are flat spectra without a characteristic peak.

Figure 6:
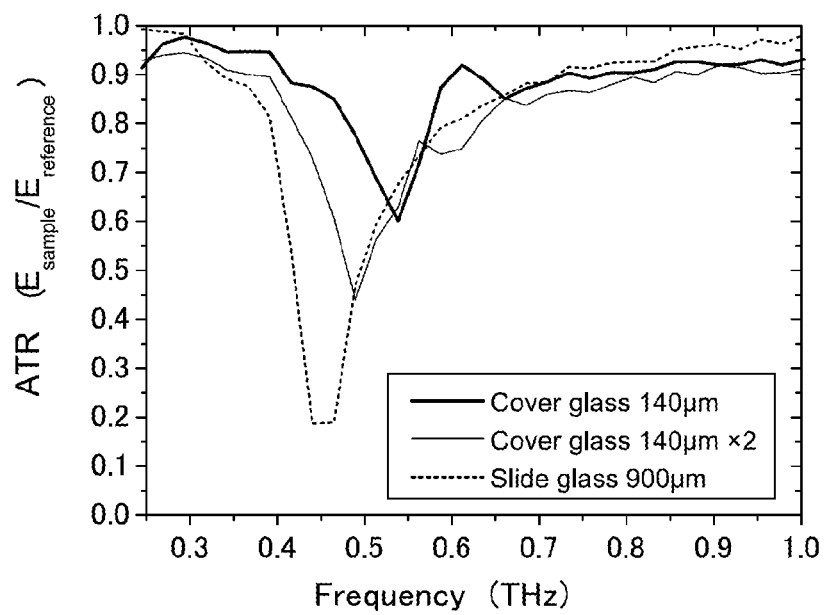
FIG. 6 is a graph showing an example of measurement results in relation to changes in thickness of a base plate.

FIG. 6 shows an example of measurement results of terahertz wave spectra measured with the terahertz wave measurement device 10 according to the first exemplary embodiment, in a state in which the sample 50 is not disposed on the base plate 12. In the example in FIG. 6, the period g of the conductive periodic structure 14 is 120 µm, the aperture width o is 60 µm and the thickness of the base plate 12 is, respectively, 140 µm (a single cover glass), 280 µm (two 140 µm thickness cover glasses), or 900 µm (one slide glass).

As shown in FIG. 6, in each terahertz wave spectrum measured by the terahertz wave measurement device 10 according to the first exemplary embodiment, a dip is formed in a certain frequency region. The frequency region in which the dip is formed (hereinafter referred to as the "dip frequency") shifts to the low-frequency side as the thickness of the base plate 12 increases. In the example in FIG. 6, the dip frequency is 0.5382 THz when the thickness of the base plate 12 is 140 µm, 0.4892 THz when the thickness is 280 µm, and 0.4403 THz when the thickness is 900 µm. This result indicates that the dip frequency reacts sensitively to conditions in the vicinity a few hundred µm from the surface of the conductive periodic structure 14.

It has been reported that the cause for a single dip in the spectrum is surface waves on the conductive periodic structure (Reference Document: T. Okada, K. Ooi, Y. Nakata, K. Fujita, K. Tanaka, and K. Tanaka, Optics Letters, 35 (2010), 1719). For a conductive wire grid structure in which the conductive periodic structure is thin, using the modal expansion method, a dispersion relationship of these surface waves can be represented as in the following expression (1).

$$f_{dip} = c/(g \times (\sqrt{\epsilon} \sin\theta + 1)) \qquad (1)$$

In this expression, $f_{dip}$ represents the dip frequency, c represents the speed of light in a vacuum, g represents the period of the conductive periodic structure, $\epsilon$ represents the refractive index of the waveguide 16 (the prism), and θ represents an incidence angle corresponding to total reflection. For example, if g is 120 µm, $\sqrt{\epsilon}$ is 3.42 and θ is 51.6°, the obtained dip frequency $f_{dip}$ is 0.679 THz.

Figure 7:
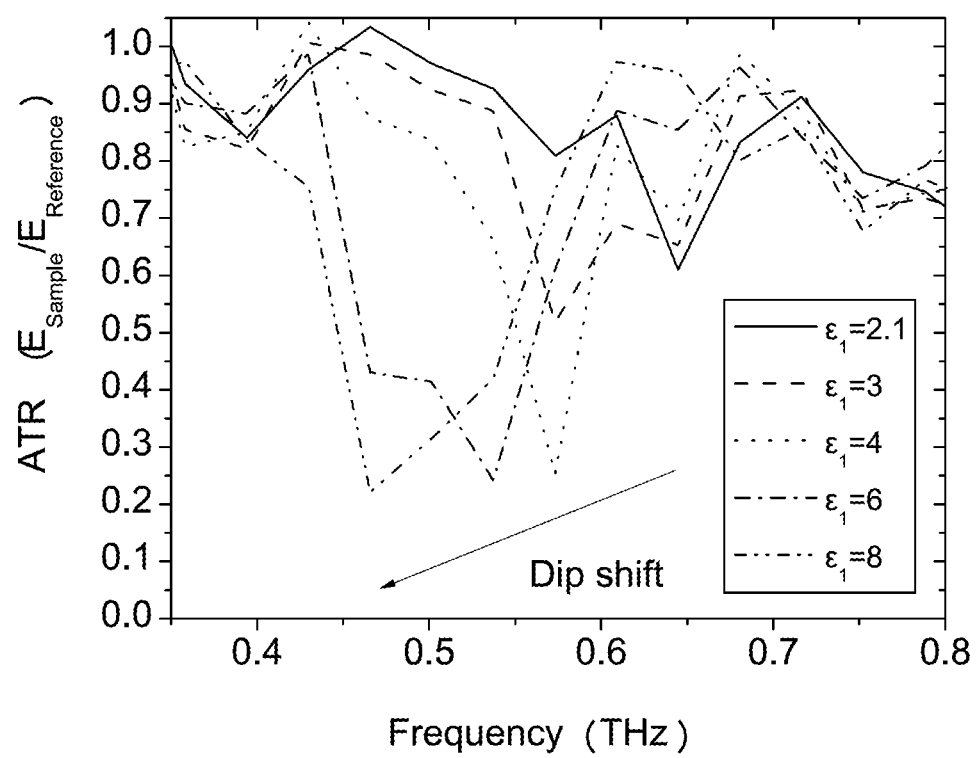
FIG. 7 is a graph showing finite difference time domain (FDTD) simulation results in relation to changes in dielectric constant of the base plate.

FIG. 7 shows the results of simulations with a finite difference time domain method (FDTD) of spectra when a dielectric constant $\epsilon_1$ of the base plate 12 is altered. As shown in FIG. 7, as the dielectric constant $\epsilon_1$ of the base plate 12 increases, the dip frequency shifts to the low-frequency side and the ATR at the dip frequency falls (i.e., the dip becomes deeper).

Thus, the dip frequency and the shape of the dip may be controlled by the period of the conductive periodic structure 14, the thickness of the base plate 12, properties of the base plate 12 (the dielectric constant or refractive index) and suchlike.

Figure 8:
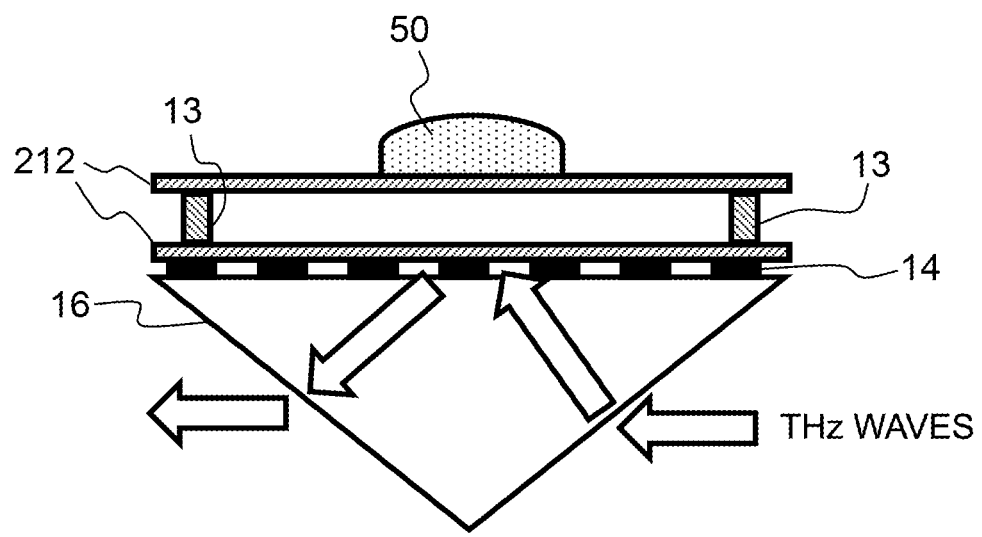
FIG. 8 is a schematic diagram showing another structure of the terahertz wave measurement device.
Figure 9:
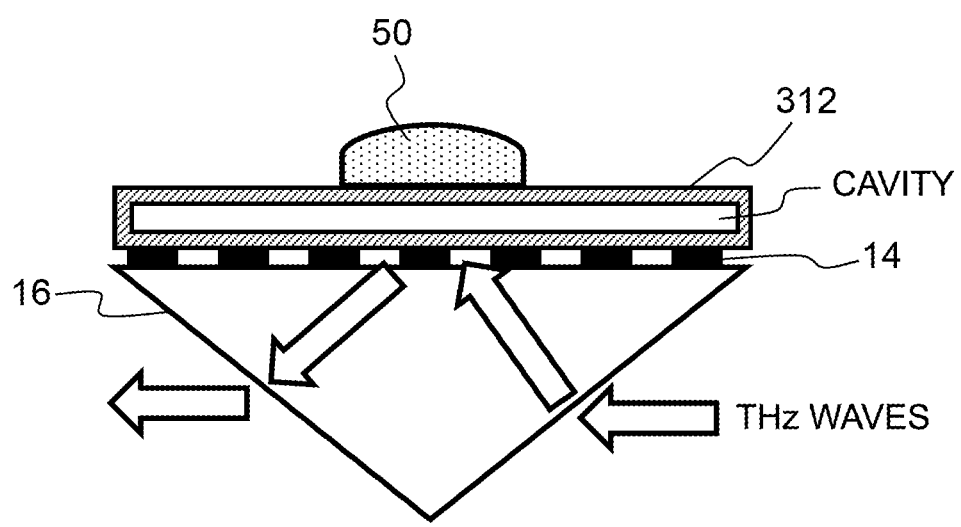
FIG. 9 is a schematic diagram showing yet another structure of the terahertz wave measurement device.
Figure 10:
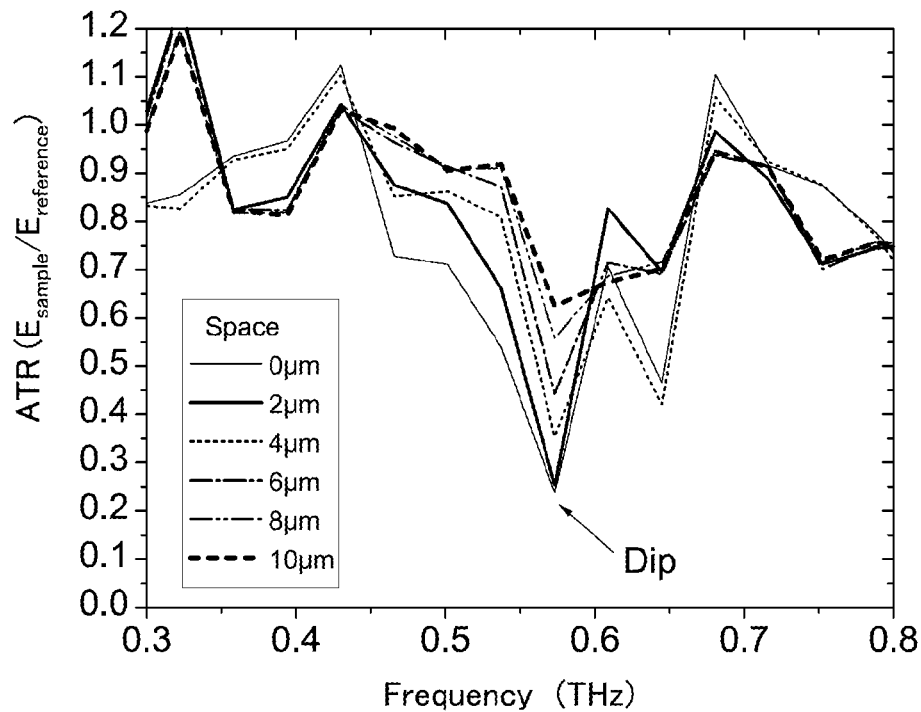
FIG. 10 is a graph showing FDTD simulation results in relation to changes in a distance between a position at which a sample is disposed and the conductive periodic structure.
Figure 11:
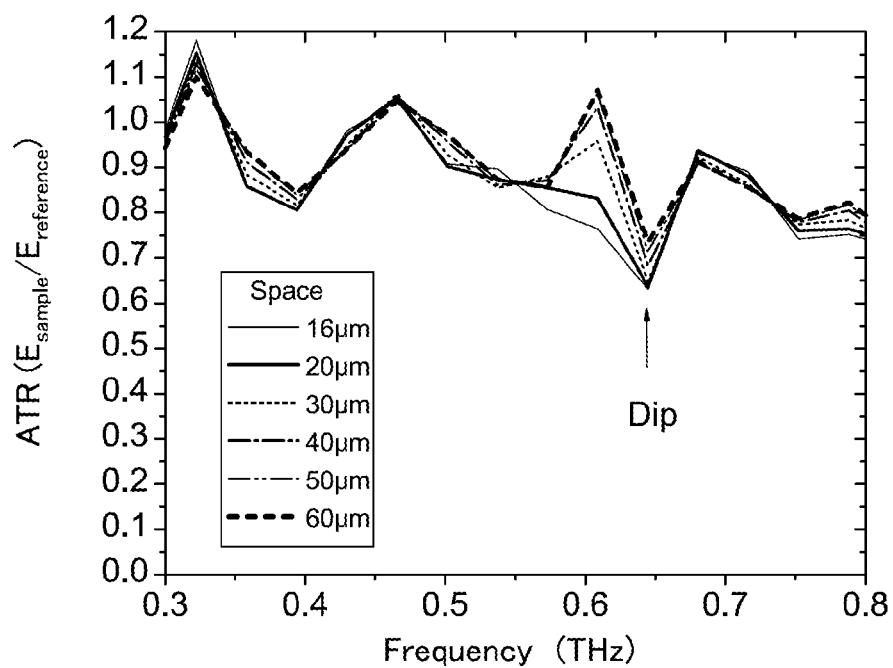
FIG. 11 is a graph showing FDTD simulation results in relation to changes in the distance between the position at which the sample is disposed and the conductive periodic structure.

Here, a case has been described in which the base plate 12 and the conductive periodic structure 14 are put into area contact, and a distance between a position at which the sample 50 is disposed and the conductive periodic structure 14 is controlled by the thickness of the base plate 12, but this is not limiting. For example, as shown in FIG. 8, spacers 13 may be disposed between a base plate 212 disposed on the conductive periodic structure 14 and a base plate 212 on which the sample 50 is disposed. As shown in FIG. 9, a base plate 312 inside which a cavity is formed may also be used. FIG. 10 and FIG. 11 show the results of simulations with FDTD of spectra when the distance between the position at which the sample 50 is disposed and the conductive periodic structure 14 is altered. As shown in FIG. 10 and FIG. 11, the ATR at the dip frequency falls (the dip becomes deeper) as the distance between the position at which the sample 50 is disposed and the conductive periodic structure 14 is reduced.

Figure 12:
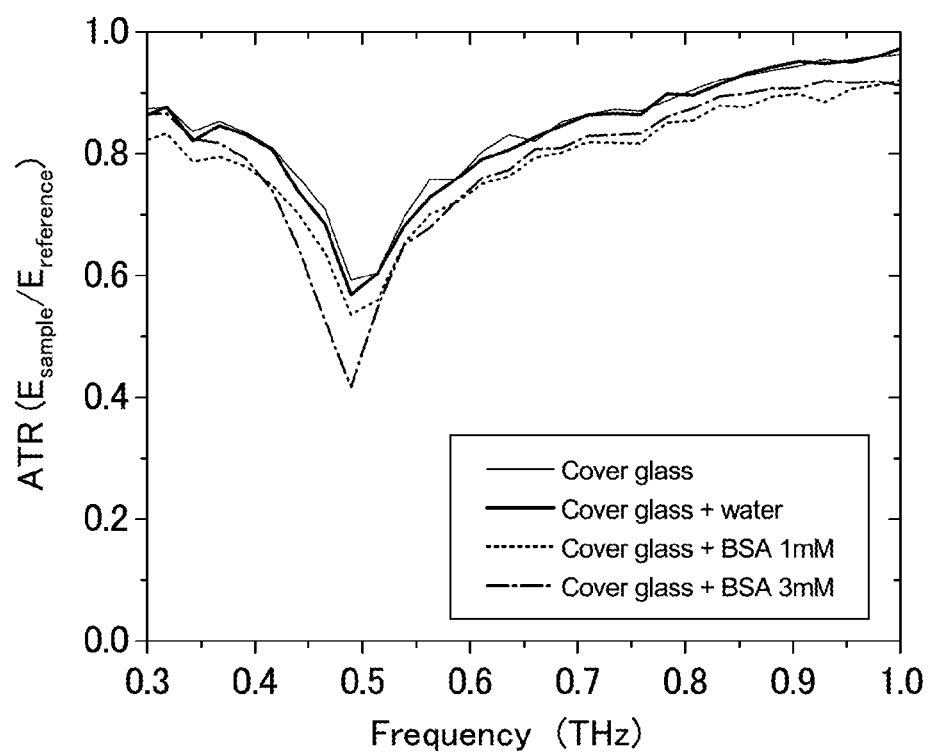
FIG. 12 is a graph showing an example of measurement results in relation to changes in concentration of BSA.

FIG. 12 shows terahertz wave spectra in solutions in accordance with changes in the concentration of BSA (no sample, 0 mM (i.e., water), 1 mM and 3 mM), measured using the terahertz wave measurement device 10 with the period g of the conductive periodic structure 14 set to 120 µm and the aperture width o set to 60 µm. As the BSA concentration increases, the ATR at the dip frequency falls. In the example of FIG. 12, the ATR is 0.569 when the BSA concentration is 0, the ATR is 0.536 when the BSA concentration is 1 mM, and the ATR is 0.417 when the BSA concentration is 3 mM. Changes in ATR respond more sensitively to the concentration of BSA at the dip frequency than at frequencies other than the dip frequency. This result indicates that there is more sensitivity at the dip frequency than at other frequencies. However, the dip frequency itself does not shift with changes in the concentration of BSA. This result indicates that shifts in the dip frequency do not occur in response to foreign substances.

Now, a terahertz wave measurement method using the terahertz wave measurement device 10 in accordance with the first exemplary embodiment is described.

First, the terahertz wave measurement device 10 according to the first exemplary embodiment is used to measure at least one of an amplitude spectrum and a phase spectrum of terahertz waves relating to a reference sample containing a binder that specifically binds to a measurement target substance, and this spectrum is used as a reference spectrum. A dip in accordance with the period of the conductive periodic structure 14, the thickness of the base plate 12, the properties of the base plate (dielectric constant and refractive index) and suchlike is formed in the reference spectrum.

Then, the same terahertz wave measurement device 10 is used to measure the at least one of the amplitude spectrum and phase spectrum of terahertz waves relating to a target sample in which the measurement target substance is added to the reference sample or a target sample for which it is unknown whether or not the measurement target substance is contained. This spectrum is used as a target spectrum. Depending on the presence or absence or content amount of the measurement target substance, a shift in the dip frequency or a change in the ATR or phase difference at the dip frequency appears in the target spectrum in accordance with an interaction between the binder and the measurement target substance.

Using this shift in the dip frequency or change in ATR or phase difference at the dip frequency, the dip frequency and ATR or phase difference at the dip frequency in the reference spectrum are compared with the dip frequency and ATR or phase difference at the dip frequency in the target spectrum. Hence, the presence of the measurement target substance is detected, a type of the measurement target substance is identified, or a property such as the concentration of the measurement target substance is analyzed.

As described hereabove, according to the terahertz wave measurement device in accordance with the first exemplary embodiment, a dip may be formed in a spectrum of terahertz waves measured by total reflection in an ATR technique using terahertz waves, because a conductive periodic structure in which aperture portions are arrayed with a predetermined period is disposed at the total reflection surface of the terahertz waves. Further, the dip frequency and the shape of the dip or the like may be controlled by optimizing a distance between the position at which a sample is disposed and the conductive periodic structure, a property of the base plate (dielectric constant or refractive index), the period of the conductive periodic structure, and the like. Thus, because based on the ATR technique, and dip is formed in a terahertz wave spectrum there is no need for labelling of a measurement target, the terahertz waves may be measured with high sensitivity, and measurement is applicable even when a sample is in the form of an aqueous solution.

The structure of the terahertz wave measurement device according to the first exemplary embodiment is provided with a spacer of tens or hundreds of pm between the total reflection surface and the sample (a reaction field of the interaction between a binder and the measurement target sample). Therefore, a noise component that is caused by non-specific adsorption of foreign substances to a sensing boundary surface may be suppressed.

—Second Exemplary Embodiment—

Now, a terahertz wave measurement device in accordance with a second exemplary embodiment is described. In the terahertz wave measurement device according to the second exemplary embodiment, portions that are the same as in the terahertz wave measurement device 10 according to the first exemplary embodiment are assigned the same reference numerals, and are not described in detail.

Figure 13:
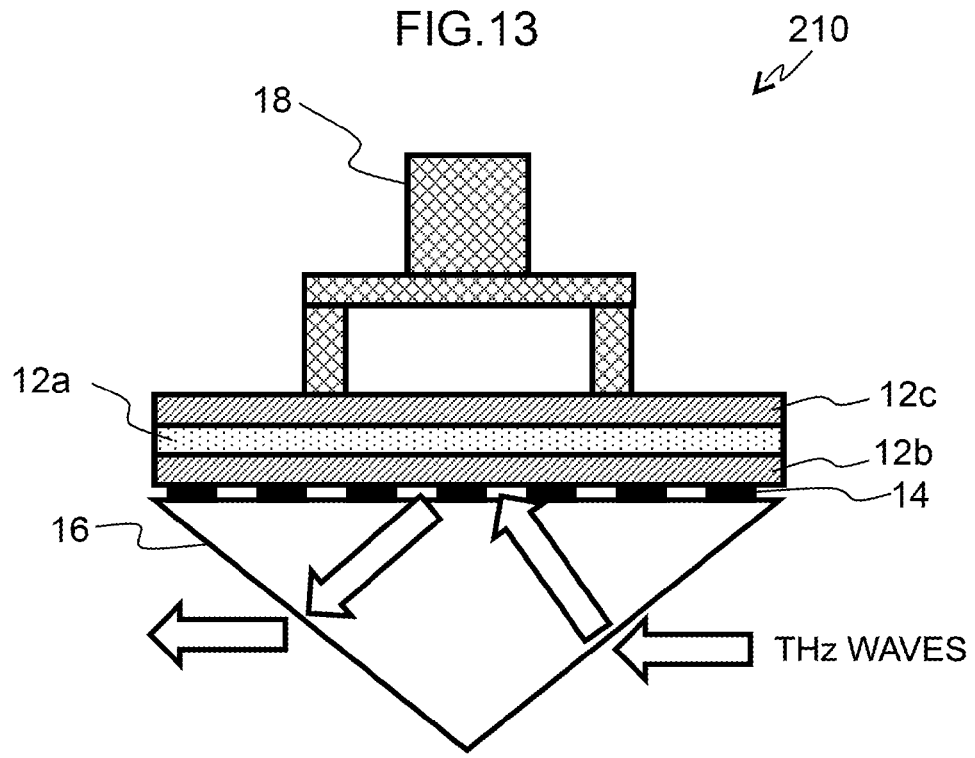
FIG. 13 is a schematic diagram showing a structure of a terahertz wave measurement device in accordance with a second exemplary embodiment.

As shown in FIG. 13, a terahertz wave measurement device 210 according to the second exemplary embodiment includes a micro-total analysis system (micro-TAS) 12a, base plates 12b and 12c, the conductive periodic structure 14, the waveguide 16 and the torque wrench 18. The micro-TAS 12a is provided with a channel thereinside through which the sample 50 can flow. The base plates 12b and 12c are disposed so as to sandwich the micro-TAS 12a. That is, the portion that is the base plate 12 in the terahertz wave measurement device 10 according to the first exemplary embodiment is structured as an arrangement of the base plate 12b, the micro-TAS 12a and the base plate 12c, in this order.

It is sufficient that the micro-TAS 12a have the property of being transmissive to terahertz waves. Specifically, if polyethylene is used, the thickness of the micro-TAS 12a may be made thinner than in a case in which glass is used.

For the second exemplary embodiment, a structure in which the micro-TAS 12a is sandwiched by the base plates 12b and 12c is described. However, a structure that uses only the micro-TAS 12a may be formed in place of the base plate 12 of the terahertz wave measurement device 10 according to the first exemplary embodiment.

A terahertz wave measurement method using the terahertz wave measurement device 210 according to the second exemplary embodiment is the same as the terahertz wave measurement method using the terahertz wave measurement device 10 according to the first exemplary embodiment, so is not described.

As described hereabove, according to the terahertz wave measurement device in accordance with the second exemplary embodiment, in addition to the effects according to the terahertz wave measurement device in accordance with the first exemplary embodiment, because the micro-TAS is used, an amount of sample to be used may be reduced.

Further, according to the technology of the present exemplary embodiment, an electric field strengthening effect in a region of a few hundred pm in the vicinity of the conductive periodic structure may be produced, and a sensing region several hundred pm wide in a depth direction may be employed. Therefore, an arrangement of the channels in the micro-TAS may be designed with significant freedom.

EXAMPLE 1

An Example 1 relating to the terahertz wave measurement device 10 according to the first exemplary embodiment is described.

Figure 14:
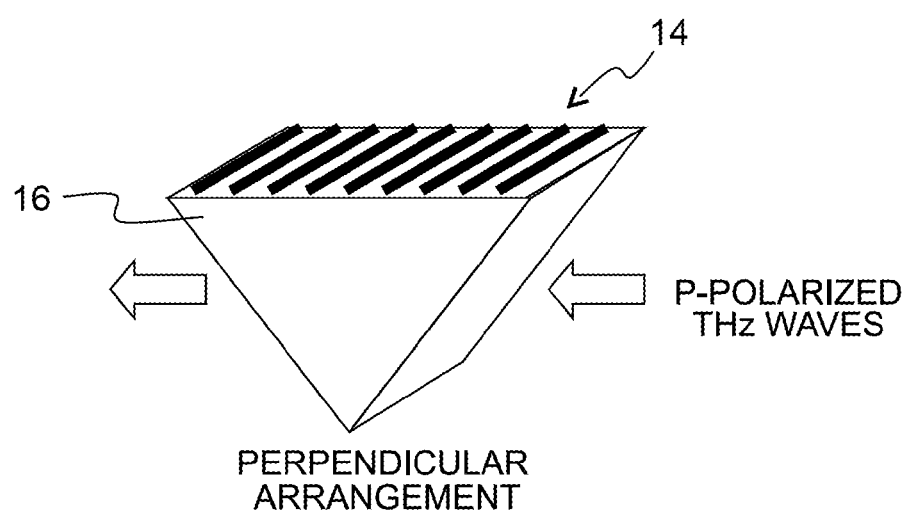
FIG. 14 is a schematic diagram for describing a perpendicular arrangement of the conductive periodic structure.

In Example 1, in the structure shown in FIG. 1, a wire grid of stainless steel (SUS 304) is used as the conductive periodic structure 14. The period g of the wire grid is 120 μm, the aperture width o is 60 μm and the thickness is 50 μm. The orientation of the wire grid is arranged to be perpendicular to a direction of propagation of p-polarized terahertz waves, as illustrated in FIG. 14. A high-resistance silicon Dove prism (10 kΩ•cm) is used as the waveguide 16. A cover glass with a thickness of approximately 105 μm (MAS COATING, fabricated by Matsunami Glass Ind. Ltd.) is used as the base plate 12. The wire grid is disposed on the Dove prism, and the cover glass is disposed on the wire grid. The Dove prism, the wire grid and the cover glass are fixed in area contact by the torque wrench 18 at 20 N•m. To assure a measurement region, the torque wrench 18 has a hollow structure with a diameter of 5 mm. In a spectrum of terahertz waves measured without placing the sample 50 on the base plate 12 under these conditions, a dip frequency of 0.526 THz is obtained.

In the terahertz wave measurement device according to Example 1, a lectin (ConA) is used as a binder, and a sugar chain (glycogen or dextran) is used as a sample. Interactions between the lectin and the sugar chains are measured from the terahertz wave spectra. Each sample was prepared by the following process.

A cover glass was coated with amino groups, immersed in a 0.1 mg/ml solution of ConA for 30 minutes, and then rinsed with ultrapure water for 5 minutes. Then the cover glass was immersed respectively in a phosphate-buffered solution (hereinafter referred to as "PBS") of 0.1 mg/ml glycogen, a PBS of 0.1 mg/ml dextran, a PBS of 0.1 mg/ml BSA, or a PBS of 0.1 mg/ml glycogen and 0.1 mg/ml BSA, and then washed with ultrapure water for 5 minutes.

Figure 15:
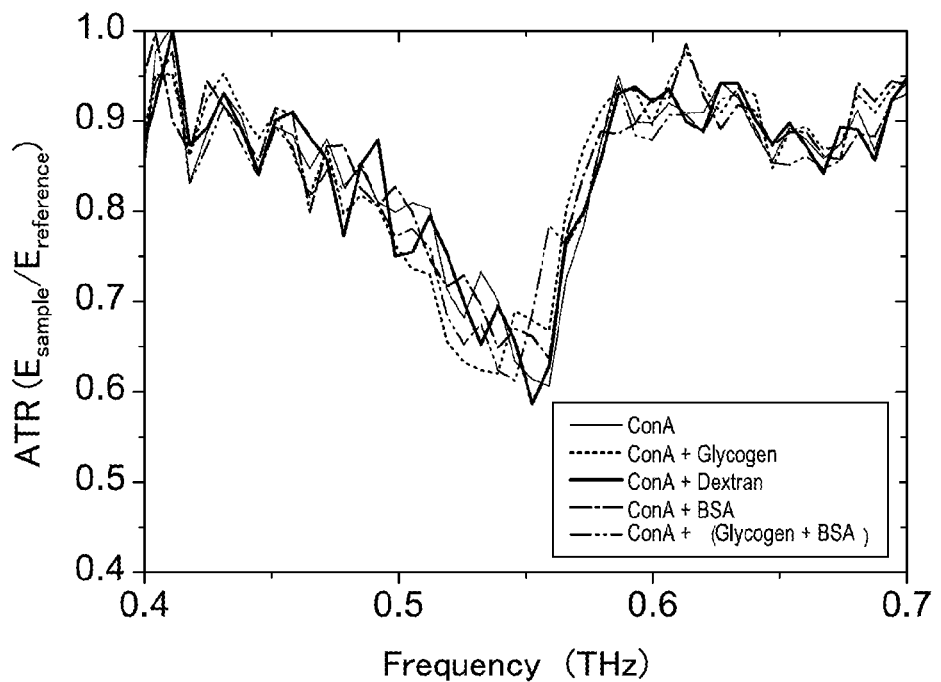
FIG. 15 is a graph showing an example of measurement results (dry samples) relating to interactions between a lectin and sugar chain in Example 1.
Figure 16:
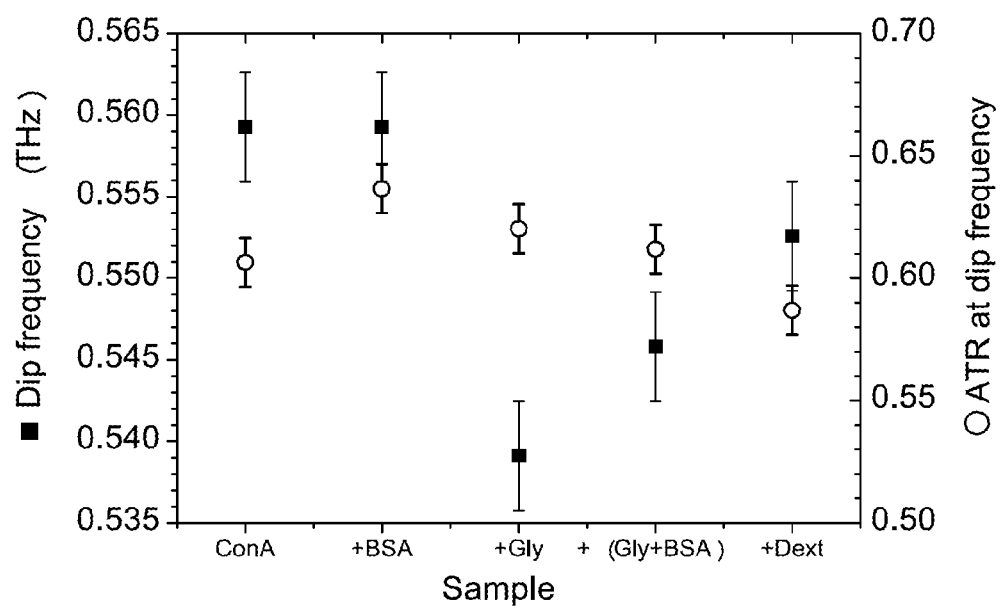
FIG. 16 is a graph showing relationships between dip frequencies in FIG. 15 and ATR at the dip frequencies.

First, each of the above samples is dried and measured. The terahertz wave measurement results are shown in FIG. 15. Relationships between the dip frequencies in FIG. 15 and the ATR at these dip frequencies are shown in FIG. 16. Comparing with the condition of ConA alone (0.5593 THz), the dip frequency with specific binding between ConA and glycogen shifts to the low-frequency side (0.5391 THz). This is probably because there is an vibration mode of specific binding between ConA and glycogen in the terahertz range. Comparing with the condition of ConA alone, the dip frequency with non-specific adsorption between ConA and BSA does not shift (0.5593 THz). This is probably because ConA and BSA do not specifically bond, or if they do bond they only do so in small amounts.

Comparing with the condition of ConA alone (0.5593 THz), the dip frequency with a reaction between ConA and the mixture of glycogen and BSA shifts to the low-frequency side (0.5458 THz). In the context of terahertz wave detection, it is desirable to distinguish specific binding from background effects such as external substances. This result indicates that the specific binding between ConA and glycogen can be detected even when foreign substances such as BSA is mixed in.

Comparing with the condition of ConA alone (0.5593 THz), the dip frequency with the specific binding between ConA and dextran shifts to the low-frequency side (0.5526 THz), but the shift amount is smaller than that of the dip frequency with the specific binding between ConA and glycogen (0.5391 THz). It is known that the binding force between ConA and dextran (binding constant: $1.5 \times 10^4$ $M^{-1}$) is smaller than the binding force between ConA and glycogen (binding constant: $1.48 \times 10^6$ $M^{-1}$), and this result is probably due to a quantity of bonds between ConA and glycogen being greater than a quantity of bonds between ConA and dextran.

Figure 17:
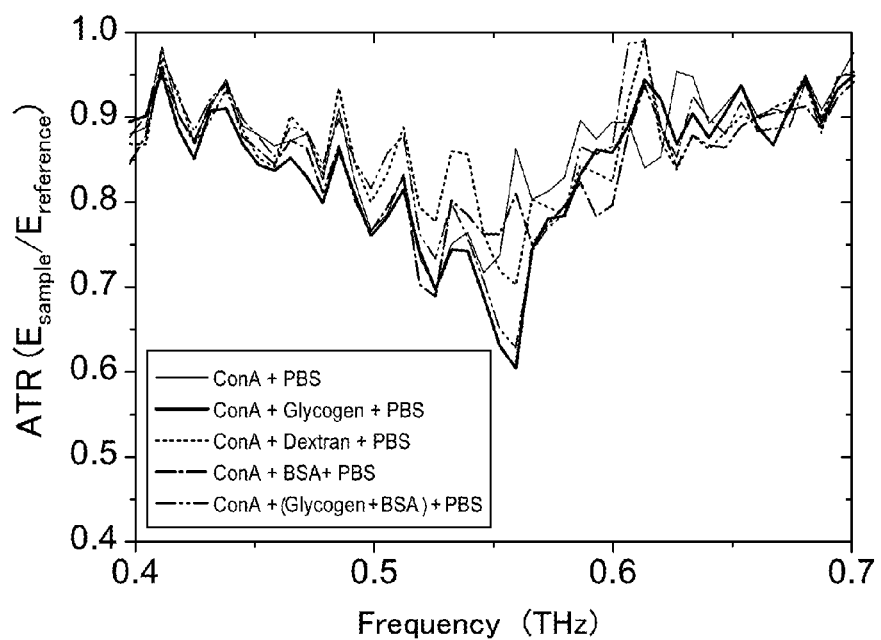
FIG. 17 is a graph showing an example of measurement results (of PBS solutions) relating to interactions between the lectin and sugar chain in Example 1.
Figure 18:
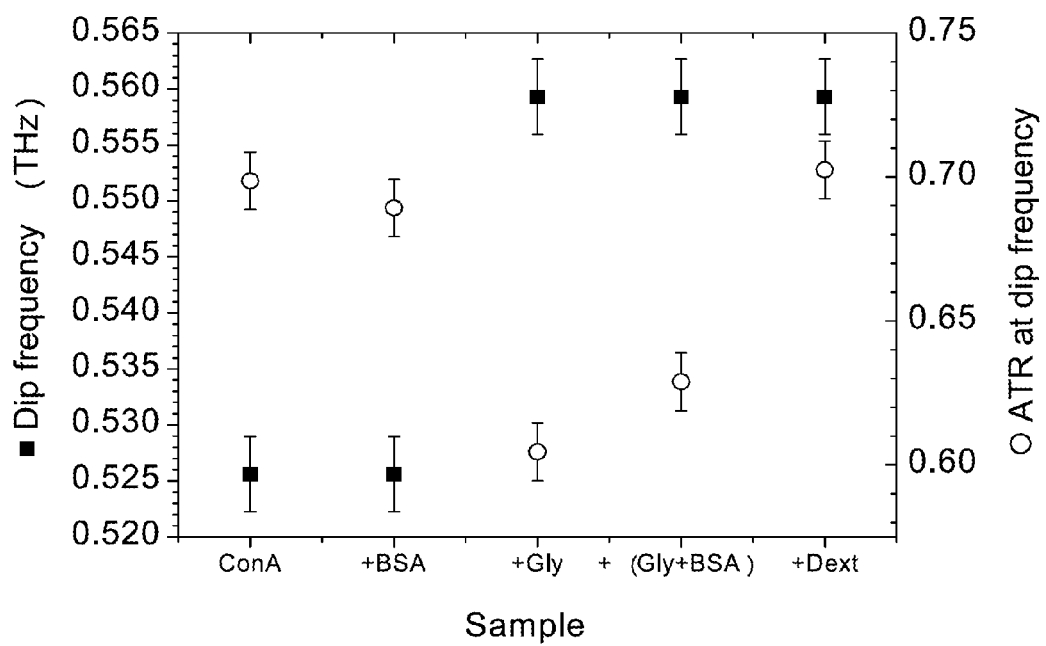
FIG. 18 is a graph showing relationships between dip frequencies in FIG. 17 and ATR at the dip frequencies.

Next, each of the above samples is measured in an aqueous solution of 50 μl of PBS, and the terahertz wave measurement results are shown in FIG. 17. Relationships between the dip frequencies in FIG. 17 and the ATR at these dip frequencies are shown in FIG. 18. Comparing with the condition of ConA alone (0.5256 THz), the dip frequency of the PBS solution with the specific binding between ConA and glycogen shifts to the high-frequency side (0.5593 THz). This is probably because there is an vibration mode of the specific binding between ConA and glycogen in the aqueous solution in the terahertz range, and localization of the hydration water contributes to the binding between ConA and glycogen. The dip frequency probably shifts to the high-frequency side because of the binding between ConA and glycogen and hydration of the surface of the cover glass.

Figure 19:
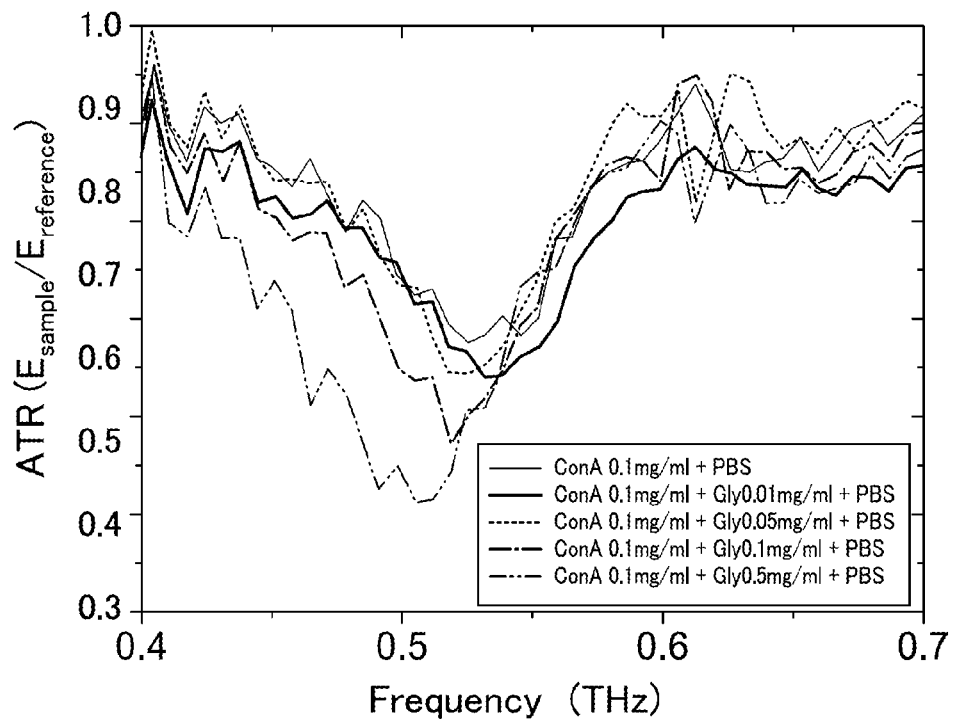
FIG. 19 is a graph showing an example of measurement results (of PBS solutions) relating to an interaction between the lectin and glucose in Example 1, with the concentration of glucose being altered.
Figure 20:
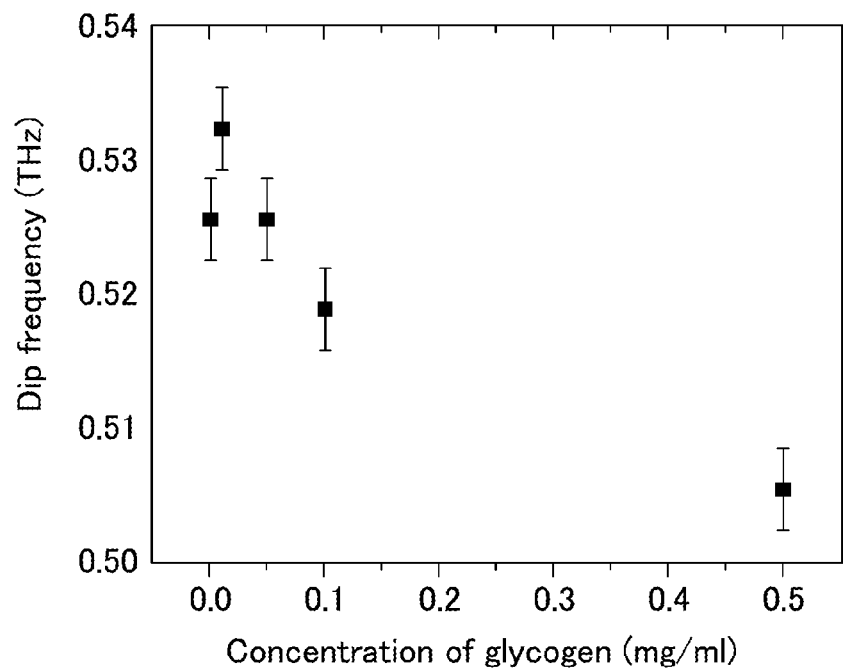
FIG. 20 is a graph showing dip frequencies in FIG. 19.

In a state in which ConA has a fixed concentration of 0.1 mg/ml in the PBS solution, the concentration of glycogen is altered (0.01 mg/ml, 0.05 mg/ml, 0.1 mg/ml, and 0.5 mg/ml), and terahertz wave measurement results relating to the interaction between ConA and glycogen are shown in FIG. 19. The dip frequencies in FIG. 19 are shown in FIG. 20. With a low concentration of glycogen (0.01 mg/ml), the dip frequency shifts to the high-frequency side, whereas with a high concentration of glycogen (from 0.05 mg/ml), the dip frequency shifts to the low-frequency side. For the low-concentration glycogen, this is probably because localization of water contributes to the binding between ConA and glycogen. The shift of the dip frequency to the high-frequency side is probably because of the binding between ConA and glycogen and hydration of the surface of the cover glass. For the high-concentration glycogen, there is an vibration mode of the specific binding between ConA and glycogen in the terahertz range. Therefore, the shift of the dip frequency to the low-frequency side is probably because a refractive index is increased by the binding between ConA and glycogen.

Figure 21:
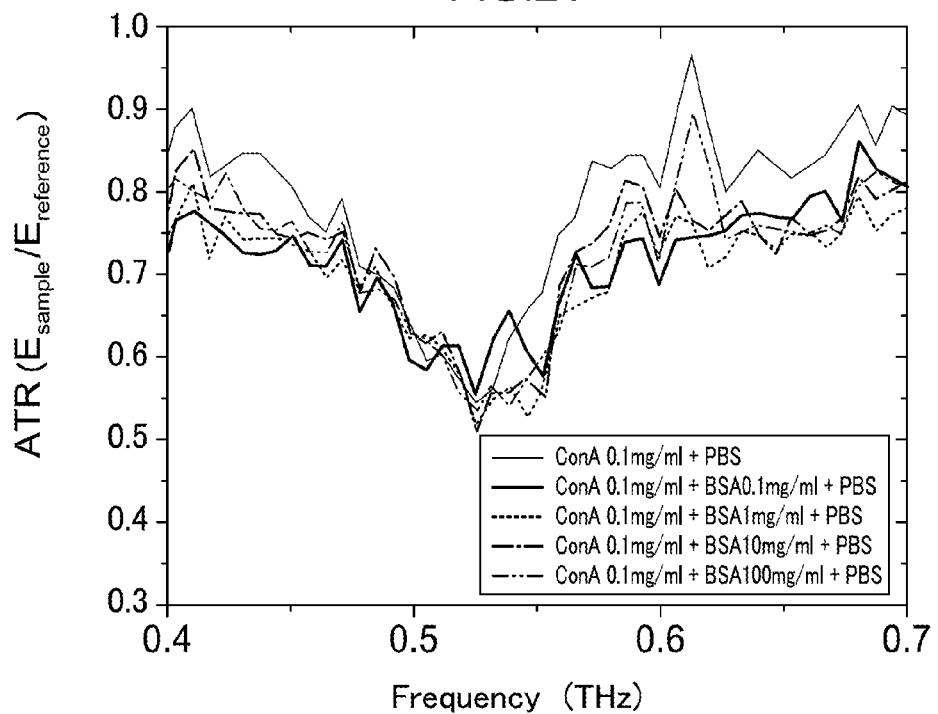
FIG. 21 is a graph showing an example of measurement results in relation to changes in a concentration of BSA in Example 1.

In a state in which ConA has a fixed concentration of 0.1 mg/ml in the PBS solution, the BSA concentration is altered (0.1 mg/ml, 1.0 mg/ml, 10 mg/ml, and 100 mg/ml), and terahertz wave measurement results relating to the interaction between ConA and BSA are shown in FIG. 21. The dip frequency does not shift even though the BSA concentration increases. This is probably because ConA and BSA do not specifically bond, or if they do bond they only do so in small amounts.

EXAMPLE 2

An Example 2 relating to the terahertz wave measurement device 210 according to the second exemplary embodiment is described.

In Example 2, as shown in FIG. 13, a micro-TAS made of polyethylene with an overall thickness of 140 μm is sandwiched from above and below by cover glasses the same as that in Example 1. The micro-TAS is structured by layers (a laminate) of a top plate, a channel and a base plate. The material of the top plate and the base plate is polyethylene, and the thicknesses thereof are 53 μm. The channel is made of polyethylene terephthalate (PET) and an acrylic adhesive, and has a thickness of 34 μm. A measurement region in the micro-TAS has a diameter of 4 mm. Other structures are the same as in Example 1. In a spectrum of terahertz waves measured without the sample 50 flowing in the micro-TAS under these conditions, a dip frequency of 0.505 THz is obtained.

In the terahertz wave measurement device according to Example 2, a lectin (ConA) is used as the binder and a sugar chain (glycogen) is used as the sample The interaction between the lectin and the sugar chain is measured from terahertz wave spectra. Each sample was prepared by the following process.

ConA at a concentration of 0.1 mg/ml in a PBS solution was injected into the micro-TAS for 1 hour and extracted by a pump, after which the micro-TAS was rinsed with PBS solution. Then, 10 mg/ml of MPC polymer for blocking was injected into the micro-TAS for 10 minutes. The blocking MPC polymer is a biorelated substance such as a hydrophilic phospholipid polymer. Here, the blocking MPC polymer is used as a protective liquid for the inside of the micro-TAS channel The blocking MPC polymer was removed by a pump, after which the micro-TAS was rinsed with PBS solution. Then, glycogen at a concentration of 0.01 mg/ml or 0.05 mg/ml in a PBS solution was injected into the micro-TAS for 1 hour and removed by a pump, after which the micro-TAS was rinsed with PBS solution, and PBS solution was injected into the micro-TAS.

Figure 22:
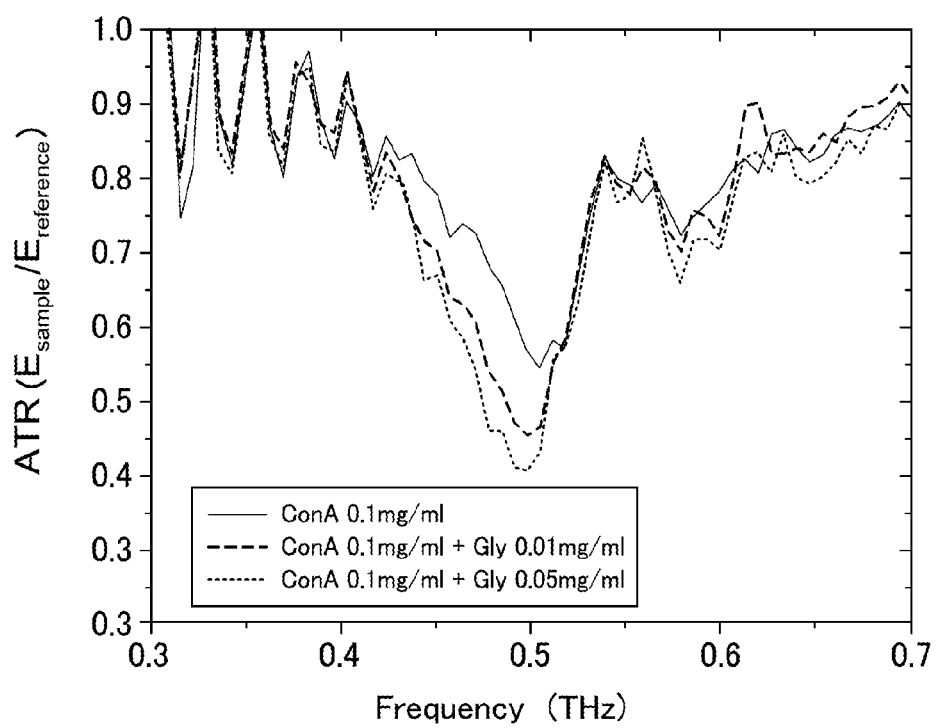
FIG. 22 is a graph showing an example of measurement results (of PBS solutions) relating to the interaction between lectin and glucose in Example 2, with the concentration of glucose being altered.

Terahertz wave measurement results relating to the interaction between ConA and glycogen in the micro-TAS using the samples described above are shown in FIG. 22. Comparing with the condition of ConA alone (0.5054 THz), the dip frequency with the binding between ConA and glycogen shifts to the low-frequency side (0.4987 THz). The ATR at the dip frequency with a glycogen concentration of 0.05 mg/ml is smaller than the ATR at the dip frequency with a glycogen concentration of 0.01 mg/ml. This is probably become there is an vibration mode of the specific binding between ConA and glycogen in the terahertz region, so a refractive index increases with the binding between ConA and glycogen. This result indicates that specific binding between a binder and a measurement target substance in the channel of a micro-TAS that is separated by a spacing of 192 μm from the wire grid may be detected.

Figure 23:
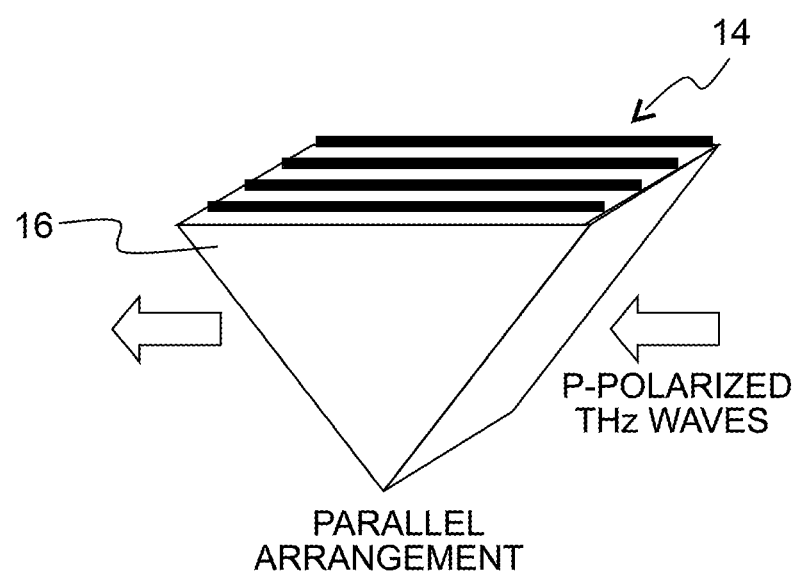
FIG. 23 is a schematic diagram for describing a parallel arrangement of the conductive periodic structure.
Figure 24:
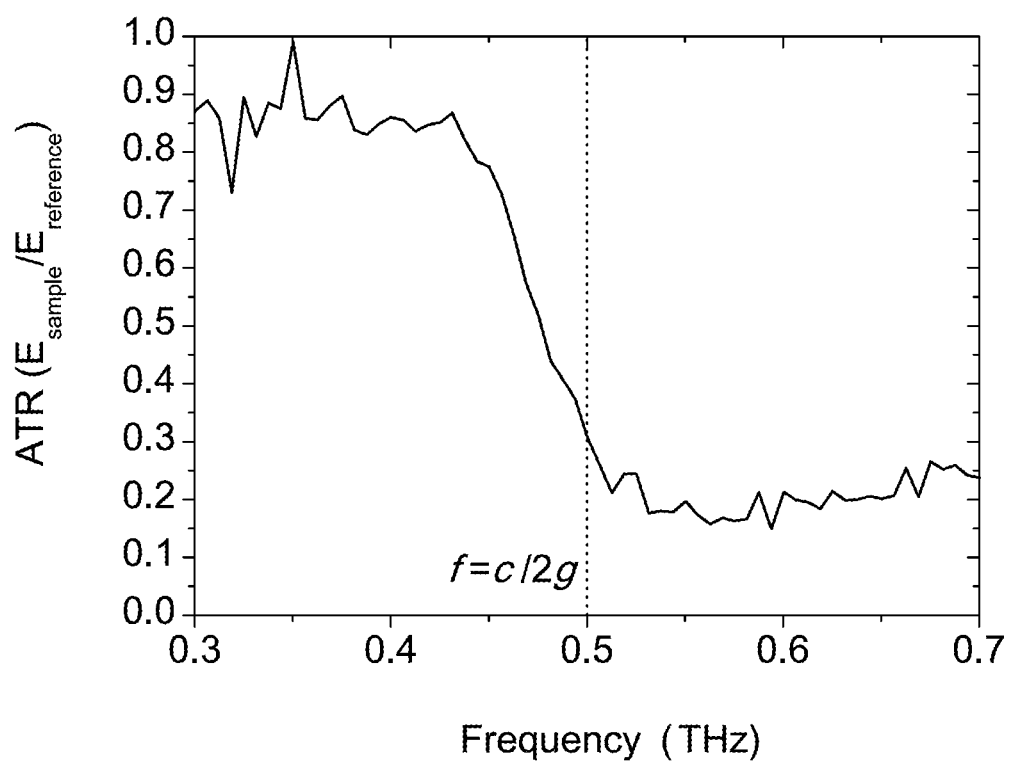
FIG. 24 is a graph showing an example of measurement results when the orientation of the conductive periodic structure is arranged to be parallel with a direction of propagation of terahertz waves.

In the exemplary embodiments and Examples described above, cases are described in which the orientation of the wire grid is arranged perpendicular to the direction of propagation of p-polarized terahertz waves. However, as shown in FIG. 23, the orientation of the wire grid may be arranged parallel to the direction of propagation of p-polarized terahertz waves. In this case, the measured terahertz waves have a spectrum, as illustrated in FIG. 24, in which the ATR rapidly falls in the vicinity of a frequency $f=c/2g$. As illustrated in FIG. 24, the frequency at which the ATR rapidly changes may be treated as a frequency that represents a characteristic absorption, similarly to the dip frequencies in the exemplary embodiments and Examples described above.

Figure 25:
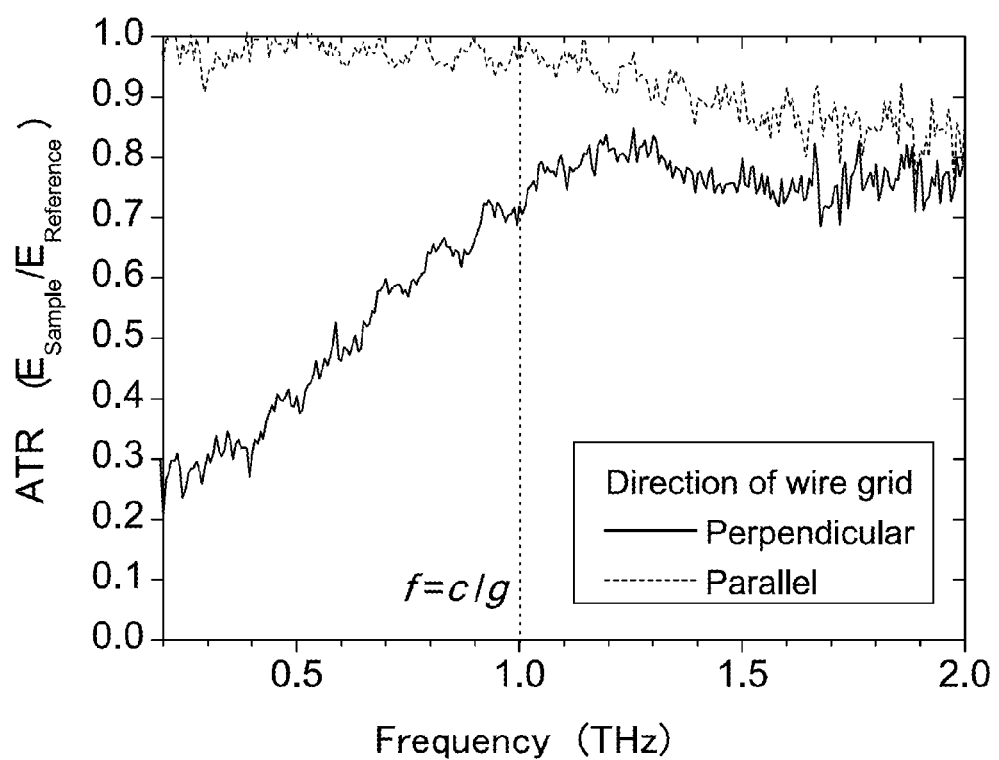
FIG. 25 is a graph showing an example of measurement results when terahertz waves are incident on the conductors in the s-polarization.

In the exemplary embodiments and Examples described above, cases are described in which terahertz waves are incident on the waveguide (prism) in the p polarization. However, the terahertz waves may be incident in the s polarization. If terahertz waves are incident in the s polarization too, the orientation of the wave grid may be arranged to be perpendicular or parallel to the direction of propagation of the terahertz waves. In these cases, the measured terahertz waves have spectra as illustrated in FIG. 25. If the orientation of the wire grid is arranged perpendicular to the propagation direction of the terahertz waves, in a characteristic spectrum the ATR increases in the vicinity of a frequency $f=c/g$.

Figure 26:
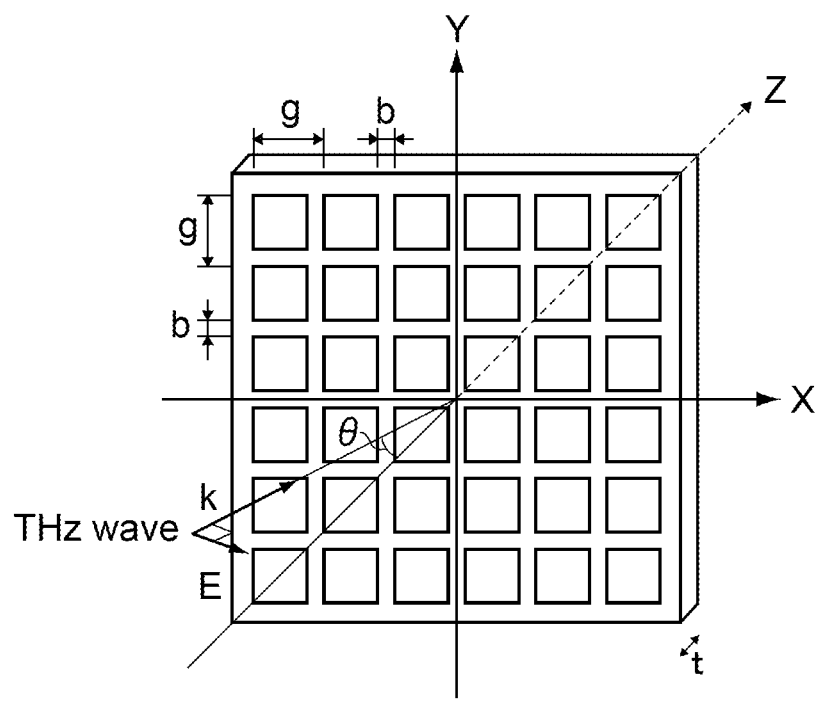
FIG. 26 is a schematic diagram showing another structure of the conductive periodic structure.

In the exemplary embodiments and Examples described above, cases are described in which an example of a conductive periodic structure is a wire grid structure, which is a structure that is periodic in one dimension. However, as illustrated in FIG. 26, the periodic conductive structure may be a metal mesh structure, which is a structure that is periodic in two dimensions. An example of measurement results if in the conductive periodic structure that is a metal mesh structure shown in FIG. 26, a period g is 302 μm, a metal member width b is 74 μm, a thickness t is 6 μm and a terahertz wave incidence angle θ is 0° is illustrated in FIG. 27. As shown in FIG. 27, a dip in the transmission spectrum is caused by obliquely incident components of the incident light. Because of a condensing apparatus, there is an obliquely incident component even when θ is 0°.

In the exemplary embodiments and Examples described above, the measurement of terahertz waves is carried out by terahertz time domain spectroscopy (THz-TDS), but may be carried out by a frequency sampling technique such as frequency difference generation or the like. In THz-TDS, information on phase is obtained at the same time as amplitude. Thus, phase information may be used for analysis as well as amplitudes. When THz-TDS is used, if designing for dip frequencies of around 3 THz or less, it is preferable to use a photoconduction antenna as a terahertz wave generation component. If designing for dip frequencies of around 3 THz or higher, it is preferable to use a DAST (4-dimethylamino-N-methyl-4-stilbazolium tosylate) crystal. A DAST crystal absorbs waves at 1.1 THz but may be used for measurements over a wide region up to around 7 THz. If a dip is to be formed in a spectrum between 3 THz and 7 THz, the period of the conductive periodic structure is set to between 27 μm and 12 μm.

In the exemplary embodiments and Examples described above, cases are described in which the base plate, the conductive periodic structure and the waveguide are respectively separate structures. However, these may be structured integrally by vapor deposition of the conductive periodic structure onto the face of the base plate opposite to the face thereof at which the sample is to be disposed, or onto the face at the total reflection surface side of the waveguide, or by printing a pattern of the conductive periodic structure onto these same. However, if the base plate, the conductive periodic structure and the waveguide are respectively separate structures as in the exemplary embodiments and Examples described above, flexible device design is possible because it is sufficient merely to exchange the conductive periodic structure or the base plate to form a desired dip in a spectrum.

The present invention may of course be applied to label-free terahertz wave measurements of dry samples and may also be applied to label-free terahertz wave measurements of interactions with biorelated substances in aqueous solutions. More specifically, the present invention is applicable to the detection of lectin micro-arrays, protein micro-arrays, DNA micro-arrays and food allergens, and to the detection of antigen-antibody reactions, the detection of interactions between biomolecules, the detection of interactions between cells and biomolecules, the detection of cell-to-cell interactions, and so forth.

What is claimed is:

1. A terahertz wave measurement device comprising:
a base plate at which a sample is to be disposed, the base plate being transmissive to terahertz waves;
a conductive periodic structure in which a plurality of transmission portions that transmit terahertz waves are arrayed with a predetermined period, at least a surface of the conductive periodic structure being constituted with a conductive material, and the conductive periodic structure being disposed apart from a position at which the sample is disposed; and
a waveguide including a total reflection surface provided at a boundary face with the conductive periodic structure, the total reflection surface totally reflecting incident terahertz waves, and the waveguide guiding incident terahertz waves in a direction toward the total reflection surface, wherein the magnitude of at least one of a distance between the position at which the sample is disposed and the conductive periodic structure, a property of the base plate, or the predetermined period is set such that terahertz waves emitted from the waveguide by total reflection at the total reflection surface show a characteristic absorption in a predetermined frequency region.

2. The terahertz wave measurement device according to claim 1, wherein the conductive periodic structure is disposed at the side of a face of the base plate that is opposite to a face thereof at which the sample is disposed.

3. The terahertz wave measurement device according to claim 1, wherein the base plate and the conductive periodic structure are disposed in area contact.

4. The terahertz wave measurement device according to claim 1, wherein at least one of the base plate and the conductive periodic structure, or the waveguide and the conductive periodic structure is integrally structured.

5. The terahertz wave measurement device according to claim 1, wherein the conductive periodic structure is sandwiched between the base plate and the waveguide, pressure is applied, and the base plate and the conductive periodic structure, and the conductive periodic structure and the waveguide are respectively put into area contact.

6. The terahertz wave measurement device according to claim 1, wherein the base plate is structured as a micro-TAS including a channel in which the sample is disposed.

7. The terahertz wave measurement device according to claim 1, wherein the conductive periodic structure includes a wire grid structure or a metal mesh structure.

8. The terahertz wave measurement device according to claim 1, wherein the waveguide includes a prism.

9. The terahertz wave measurement device according to claim 1, wherein the base plate includes glass or plastic.

10. A terahertz wave measurement method comprising:
measuring a reference spectrum using the terahertz wave measurement device according to claim 1, the reference spectrum including at least one of an amplitude spectrum or a phase spectrum of terahertz waves relating to a reference sample that includes a binder that specifically binds with a measurement target substance;
measuring a target spectrum using the terahertz wave measurement device, the target spectrum including at least one of an amplitude spectrum or a phase spectrum of terahertz waves relating to one of a target sample in which the measurement target substance is added to the reference sample, or a target sample in which a content of the measurement target substance is unknown; and
performing at least one of detection, identification or characteristic analysis of the measurement target substance on the basis of at least one of a frequency region showing a characteristic absorption or a signal strength at this frequency region in each of the reference spectrum and the target spectrum.

* * * * *